United States Patent [19]

Tolbert et al.

[11] 4,178,209
[45] Dec. 11, 1979

[54] CONTINUOUS CELL CULTURE METHOD AND APPARATUS

[75] Inventors: William R. Tolbert, Manchester; Joseph Feder, University City; Richard C. Kimes, Creve Coeur, all of Mo.

[73] Assignee: Monsanto Company, St. Louis, Mo.

[21] Appl. No.: 884,076

[22] Filed: Mar. 6, 1978

Related U.S. Application Data

[63] Continuation-in-part of Ser. No. 850,987, Nov. 14, 1977.

[51] Int. Cl.$^2$ .............................................. C12K 9/00
[52] U.S. Cl. ..................... 435/241; 195/143; 435/286
[58] Field of Search ............... 195/108, 109, 115, 119, 195/121, 127, 142, 143, 144, 1.7, 1.8

[56] References Cited

U.S. PATENT DOCUMENTS

| 328,585 | 10/1885 | Hornbostel | 195/143 X |
|---|---|---|---|
| 2,121,458 | 6/1938 | Vogelbusch | 195/143 |
| 2,530,814 | 11/1950 | Becze et al. | 195/143 |
| 2,829,931 | 4/1958 | DePree et al. | 308/36.1 |
| 2,952,588 | 9/1960 | Rinderer | 195/143 |
| 2,958,517 | 11/1960 | Harker et al. | 259/122 |
| 3,039,932 | 6/1962 | McLimans et al. | 167/78 |
| 3,241,675 | 3/1966 | Pashaian et al. | 210/73 |
| 3,572,651 | 3/1971 | Harker | 259/107 |
| 3,580,812 | 5/1971 | Bender et al. | 195/143 |
| 3,622,129 | 11/1971 | Mazowski | 259/107 |
| 3,647,632 | 3/1972 | Johnson et al. | 195/142 |
| 3,649,465 | 3/1972 | Scharf et al. | 195/143 |
| 4,025,394 | 5/1977 | Young | 195/115 |

OTHER PUBLICATIONS

Philip S. Thayer, Tissue Culture Methods and Applications, Academic Press, 1973, pp. 345–351.
H. J. Morton, In Vitro, vol. 6, pp. 89–108 (1970).
P. Himmelfarb et al., "Spin Filter Culture: The Propagation of Mammalian Cells in Suspension", Science, vol. 164, pp. 555–557; May 2, 1969.
Philip S. Thayer et al., "Effects of Perfusion with Amethopteria on L1210, Leukemia Cells in Spin Culture, Cancer Research, vol. 30, pp. 1709–1714, Jun. 1970.
R. A. Cook et al., "Use of Plastics for Suspension Cultures Vessels", In Vitro, vol. 9, No. 5, pp. 318–322; 1974.
J. Daniel Lynn et al., "Design of Large-Scale Mammilian Cell Suspension Culture Facility", Biotech. Bioeng, vol. XVII, pp. 659–673; 1975.
Andre D. Glinos et al., "Density Dependant Regulation of Growth in Suspension Cultures of L-929 Cells", Journal of Cell Physiol., vol. 79, pp. 79–90; 1971.

Primary Examiner—Raymond N. Jones
Assistant Examiner—Robert J. Warden
Attorney, Agent, or Firm—Scott J. Meyer; James W. Williams, Jr.

[57] ABSTRACT

A cell culture system and apparatus is provided for the suspension culturing of mammalian cells in which fresh media can be added and spent medium filtered and withdrawn on a continuous or semi-continuous basis without any substantial cell disruption and clogging of the filter with cell debris. The apparatus comprises a hollow flask assembly having a stationary hollow shaft means and filter unit suspended downwardly from the top thereof, and a rotatable agitator means concentrically disposed about said filter unit, said filter unit being in fluid communication with the top opening of the flask through the interior of said hollow shaft means.

5 Claims, 5 Drawing Figures

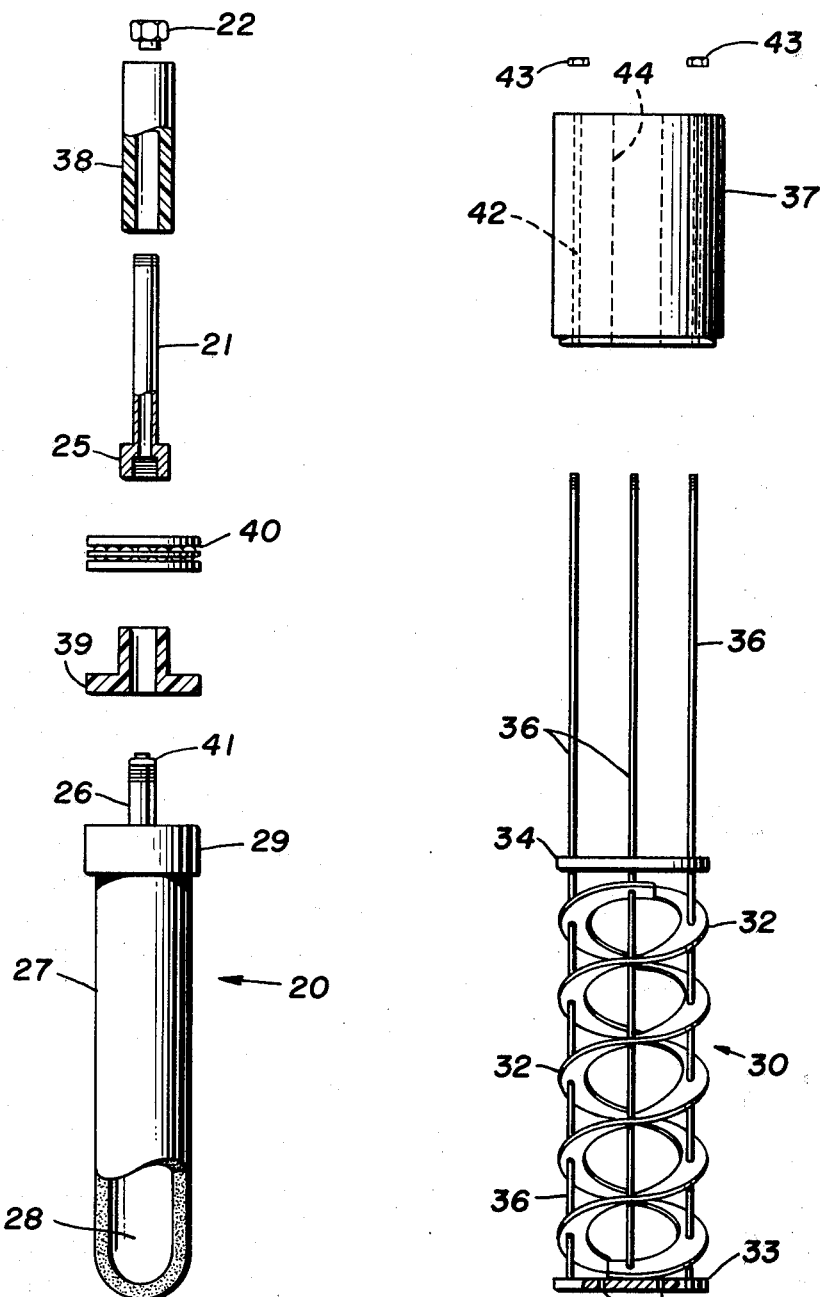

CONTINUOUS CELL CULTURE METHOD AND APPARATUS

RELATED APPLICATION

This is a continuation-in-part of copending application Ser. No. 850,987, filed Nov. 14, 1977.

BACKGROUND OF THE INVENTION

This invention relates to a continuous cell culture system and apparatus therefor. More particularly, this invention relates to a flask assembly which can be used for suspension culturing of mammalian cells in which fresh medium can be added and spent medium can be separated from the growing cells by filtration and withdrawn from the flask on a continuous or semi-continuous basis.

In recent years there has been rapid growth in the development of various methods for the culturing of mammalian cells in suspension. The attainment of high cell densities is a primary objective of many of these approaches. The use of a cell culture vessel with controlled agitation by means of a magnetic stirrer bar or mechanically driven impeller on a shaft is a typical feature of these methods. Examples of such apparatus are disclosed in U.S. Pat. Nos. 2,958,517; 3,039,932; 3,572,651; 3,622,129; and 3,649,465. These are essentially batch type spin culture devices in which the cells are incubated in a fixed amount of nutrient under appropriate culture conditions until cell growth has ceased.

It has been recognized that maintenance of constant levels of required nutrients coupled with removal of toxic cell by-products facilitates the propagation of cells in higher densities than is obtained in batch processes where the cells are grown in a fixed amount of nutrient and harvested after significant growth ceases. One approach to obtain such higher cell densities employs the batch type apparatus but involves daily centrifugation and resuspension of cells in fresh medium as reported by Glinos et al, *J. Cell Physiol.* 79, 79-90 (1971). Another approach makes use of special apparatus developed for continuous suspension cell culturing. Examples of such apparatus developed for continuous suspension cell culturing are disclosed in U.S. Pat. No. 3,647,632; by Himmelfarb, *Science* 164, 555-57 (1969); and by Thayer et al, "Tissue Culture Methods and Applications" (Kruse and Patterson, editors), Academic Press, pp. 345-51 (1973). The use of such devices in continuous cell culturing of various cell lines is further described by Thayer et al, *Cancer Res.* 30, 1709-14 (1970); Cook et al, *In Vitro* 9, 318-22 (1974); and by Lynn and Acton, *Biotech. Bioeng.* 27, 659-73 (1975).

Notwithstanding the advantages obtained with spin culture devices of the foregoing type, a problem which frequently exists is the presence of rotating bearing and seal surfaces which can contact the cells in the fluid suspension being agitated and thereby cause grinding and cell disruption at high cell densities. Placement of the rotating shaft driving means outside the culture vessel in order to avoid the grinding of cells in the flask introduces another problem, namely contamination by seepage into the vessel around the rotating shaft. Still another problem which exists with prior cell culture devices which employ filtering means is the clogging of the filter with cell debris.

BRIEF SUMMARY OF THE INVENTION

In accordance with the present invention, an improved cell culture system and apparatus is provided for the suspension culturing of cells. This system comprises culturing in a flask assembly in which fresh medium can be added and spent medium can be separated from the growing cells by filtration and withdrawn from the flask on a continuous or semi-continuous basis without any substantial clogging of the filter. In this system and apparatus, no moving bearing or seal surfaces are present in the culture fluid which could contact the cells and thereby cause cell disruption, and no rotating shaft is extended through the top of the flask which could permit contamination from the outside to enter the flask during rotation of the shaft.

The apparatus of this invention thus comprises:

(A) a hollow flask having an opening at the top.

(B) a stationary, hollow shaft means in fluid communication with said top opening and suspended downwardly therefrom.

(C) a stationary filter unit suspended downwardly from said shaft means, said filter having
 (1) a fluid collection cavity in fluid communication with the interior of said shaft means and the top opening of said flask, and
 (2) a porous peripheral surface having a pore size smaller than the cells to be cultured or the carrier particles upon which said cells are attached, and (D) a rotatable agitator means concentrically disposed about said filter unit and adapted for rotation by suspension from sleeve bearing means having low-friction engagement with said hollow shaft means.

DETAILED DESCRIPTION OF THE INVENTION

While the specification concludes with claims particularly pointing out and distinctly claiming the subject matter regarded as forming the present invention, it is believed that the invention will be better understood from the following description taken in connection with the accompanying drawings in which:

FIG. 3 is an exploded view of the filter unit of FIGS. 1 and 2 showing the hollow shaft means and its juxtaposition with portions of the sleeve assembly.

FIG. 4 is an exploded view of the agitator unit of FIGS. 1 and 2 showing its juxtaposition with portions of the sleeve assembly.

Figure 1:
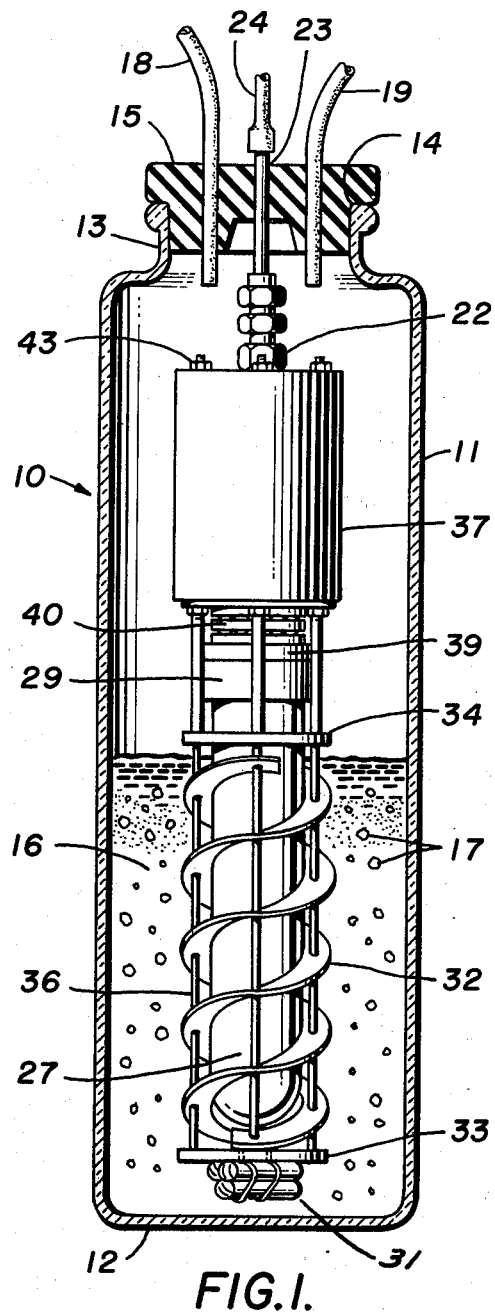
FIG. 1 is a side elevation view partly in cross section showing an embodiment of the flask assembly of the present invention.
Figure 2:
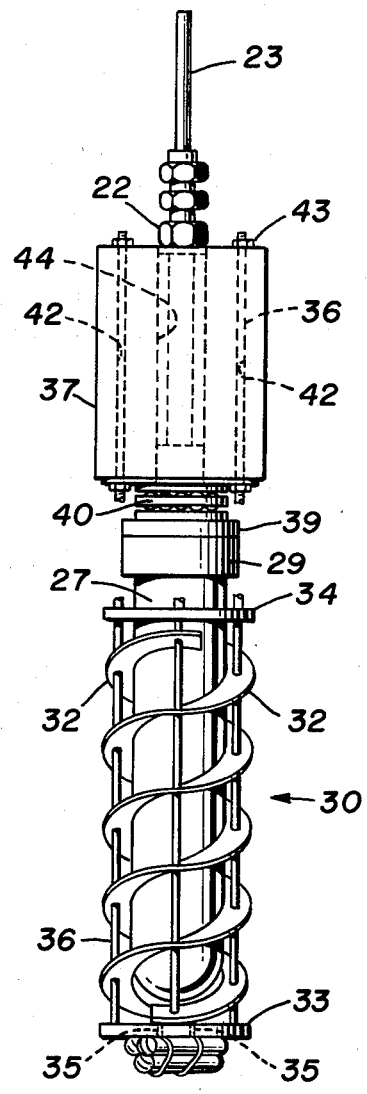
FIG. 2 is a partial side elevation view of the filter unit, agitator and sleeve assembly of FIG. 1 suspended downwardly from the tube connector means at the top.

Now with particular reference to FIGS. 1 to 4, reference numeral 10 refers generally to a flask which can be used for the continuous suspension culturing of mammalian cells. The flask preferably is made of clear glass or non-toxic rigid plastic materials but also can be made of biocompatible metals such as, for example, stainless steel. The flask is shown to have a generally cylindrical form with sidewalls 11, bottom 12, neck portion 13 and mouth 14. It will be appreciated, however, that other configurations of the flask can be employed. In FIG. 1, the mouth is shown to be closed with a removable stopper 15.

Flask 10 is shown to be partially filled with culture fluid 16 in which the cells 17 are suspended. Tubes 18 and/or 19, which pass through holes in stopper 15 and thence into the interior of the flask, lead outwardly to a source of culture medium (not shown) which can be supplied to the flask on a continuous or semi-continuous basis. These tubes, or similar such tubes, also can be used for withdrawal of cells and cell culture fluid by vertical extension below the level of the culture fluid. Additional openings and tubes also can be provided for gas inlet and outlet as may be desired.

Positioned vertically within the flask is a stationary filter unit 20 which is suspended downwardly from the top by attachment to a stationary, elongated hollow shaft 21. Shaft 21, in turn, is suspended downwardly from a connector 22 which is shown to be held by a tube portion 23 in stopper 15. The tube portion of the connector leads to conduit 24 and thence to a fluid collection reservoir (not shown). Connector 22 can be, for example, a conventional Swagelok ® union which also can be joined to an adaptor, as shown, to accommodate any specific diameter tube portion 23 or conduit 24.

Attachment of the filter unit 20 and the hollow shaft 21 is made by a threaded engagement of enlarged foot 25 of the hollow shaft and a filter conduit 26. Conduit 26 seals against shaft 21 by an elastomeric O-ring seal 41 to provide a fluid-tight engagement. Other conventional types of fluid-tight fastening means also can be used for this attachment.

Filter unit 20 is shown to have a generally cylindrical body 27 which terminates with a rounded bottom and has an internal fluid collection cavity 28 and an opening at the top 29. The filter unit body can be made of microporous porcelain, sintered stainless steel, Teflon ® plastic or other such rigid microporous filter materials. It should be understood, however, that other configurations of the filter unit also can be employed.

The pore size of the filter should be smaller than the cells to be filtered, or the carrier particles upon which the cells are attached. In cartain instances it is desired to filter all the cells. A pore size of from about $0.2\mu$ to about $7.0\mu$ is suitable for most single cells. In the case of cell aggregates or cells attached to microcarriers, the pore size can be larger but still smaller than the particles, for example, a pore size of about $25\mu$ to about $75\mu$ in the case of particles of about $100\mu$ in diameter. The carrier particles can be materials such as Sephadex ® type ion exchange beads, silica glass particles and the like substances which are known to be useful for cell attachment in the suspension culturing of mammalian cells.

In a 3- or 4-liter size cell culture flask, the commercially available Selas Flotronics ® detachable metal-connector type porcelain filter candle FDM-126 S can be conveniently used as filter unit 20 with filter conduit 26.

A rotatable agitator unit 30 is concentrically disposed about the filter unit and adapted for rotation by suspension from sleeve bearing means. The agitator unit is shown to have a double helical blade 32, a disc-shaped bottom plate 33, an annular top plate 34 and a plurality of rods 36.

Small holes 35 are drilled through the bottom plate to serve as means for removably wiring magnets 31 to the bottom of the agitator unit. Rods 36 provide means for suspending the agitator unit from the sleeve bearing means. In a preferred embodiment of the invention, four of these rods are employed in the agitator unit which are equidistantly spaced apart circumferentially for appropriate balancing of the unit.

The agitator parts can be made of stainless steel or other such suitably rigid materials which are nontoxic to the cells being propagated in the culture flask. The rigidity should be sufficient to withstand the expected forces of rotation in use of the apparatus. For example, rotation may be at about 100 to 300 rpm during operation of the cell culture system.

The sleeve bearing means is seen to comprise an outer sleeve 37, an inner sleeve 38 and a bearing seat 39. The inner sleeve is adapted for frictionally engaging the hollow shaft 21 while the outer sleeve is adapted for low-friction or relatively frictionless engagement of said inner sleeve. The bottom of outer sleeve 37 is shown to rest on an annularly flanged seat 39 with an intermediately positioned ball bearing assembly 40. The outer sleeve thus rotates with the agitator unit while the inner sleeve remains stationary with shaft 21. Use of Teflon ® plastic or plastic coated steel for the fabrication of the sleeve bearing parts provides suitable rotating bearing surfaces which require no lubrication for low-friction engagement of parts. When such platic materials, instead of steel, are also used for fabrication of shaft 21, inner sleeve 38 can be dispensed with and outer sleeve 37 can rotate directly on said shaft, with appropriate spatial modification to compensate for the absence of said inner sleeve. The rotating bearing surfaces also can be lubricated with nontoxic lubricants such as silicone grease, if desired.

Outer sleeve 37 has a central bore 44 adapted for positioning therein of the hollow shaft 21 and the interior sleeve 38. A plurality of holes 42 are equidistantly spaced apart circumferentially in outer sleeve 37 to correspondingly accommodate the plurality of agitator rods 36. Nuts 43 are used to fasten the threaded ends of rods 36 tightly against the outer sleeve.

It will be appreciated, of course, that other conventional fastening means can be used in place of those illustrated in FIGS. 1 to 4.

Figure 5:
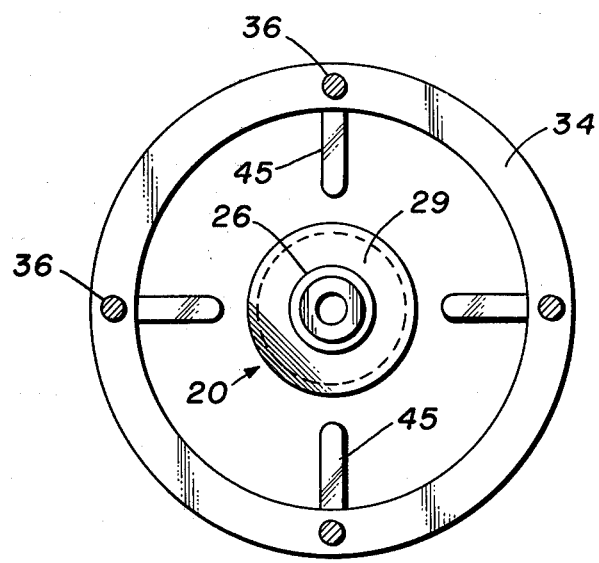
FIG. 5 is a top view of another embodiment of the agitator and filter units of the invention.

FIG. 5 is a top view which shows another embodiment of the agitator and filter units employed in the present invention. In this embodiment a plurality of elongated, flat blades 45 are substantially equidistantly spaced apart circumferentially, radiating inwardly toward the outer sidewall of the filter 20, and which extend substantially throughout the length of the filter unit, replace the double helical blades of FIGS. 1 to 4.

In still another embodiment of the invention, the annular plate 34 shown in FIG. 5 can represent the top rim of an enclosing cylinder having an outer sidewall which extends throughout the length of the filter unit. In this embodiment, the blades radiate inwardly from the inner wall of said cylinder.

In the foregoing embodiments it is preferred that the agitator blades be positioned such that they provide a relatively small clearance with the filter unit. That is, the concentric agitator should closely surround or encircle the filter, preferably substantially over the entire length of the filter. For example, when using a 3- or 4-liter capacity cell culture flask with a filter unit having a diameter of about 2 inches, use of a radial clearance around the filter of about ⅛ to ⅜ inch clearance is preferred. When using a double helical blade in these embodiments, a blade width of about ¼ to one inch and a pitch of about 30° to 80°, preferably about 45°, is eminently suitable.

The centrifugal and shear forces impending upon the cells at the interface of the rotating liquid and the stationary filter during operation of the cell culture apparatus prevent clogging of the filter. Variations in agitator configuration from the foregoing illustrative examples can be made by the person skilled in the art to maximize these shear or centrifugal effects, depending upon the type of cell suspension employed.

Thus, it shall be understood that still other modifications of the agitator blades and agitator configuration can be employed, for example, a single helical ribbon blade; or peripheral blades as in FIG. 5, but in which the angle of the blades with respect to the filter is skewed; or blades with various pitches and cross-sections other than shown in the illustrative embodiments.

In operation of the cell culture apparatus of this invention, using the embodiment of FIG. 1 for illustrative purposes, an inoculum of cells and a suitable culture medium are incubated in flask 10 under cell culture conditions which are appropriate for the particular cells used. Tubes 18 and 19 can be used to supply fresh culture medium to the flask continuously or at predetermined intervals. Magnetic bars 31 can be removably attached to the bottom of the agitator unit which can then be caused to rotate by a revolving U-shaped magnet (not shown) positioned under the cell culture flask. The filter unit is preferably suspended to a depth in the flask such that it lies completely in the fluid medium while the sleeve bearing assembly lies above the liquid level. A vacuum drawn on line 24 by a peristaltic pump (not shown), which line is in direct fluid communication with the interior of the filter unit through the intermediately disposed hollow shaft means, will cause withdrawal of fluid medium from the flask after passage through the microporous filter. Culture fluid can thus be separated from the residual cells on a continuous or semi-continuous basis. The fresh culture medium which is added through tubes 18 and 19 also can be monitored by a level controller (not shown) to maintain a constant level of suspension in the flask, if desired.

Cell culture apparatus of the present invention as described herein eliminates the usual need for a lower bearing surface in the flask below the upper level of the culture fluid. There are no moving bearing or seal surfaces in the flask assembly in contact with the suspension culture which could cause cell disruption at high cell densities. The filter unit is self-supporting and there are no moving seals between the filter unit and any filter support means which could contact the cell suspension. All seals within the filter unit are static. As no lower bearing is used, a centrally positioned solid shaft is not required within the filter unit and flow of effluent is not limited to an annular region around such shaft. The sleeve assembly which is adapted to provide suspension and allow rotation of the agitator unit concentric with the filter unit thereby facilitates the prevention of clogging of the filter with any cell debris.

The cell culture apparatus of this invention can be used with conventional auxiliary apparatus such as pumping means for pumping in fresh medium from a supply reservoir and pumping out spent media, product, and toxic materials into an effluent collection reservoir. The flask can be provided with additional openings for gas inlet and outlet, sampling tubes and probes for monitoring pH, liquid level and dissolved oxygen level. The entire flask assembly should be operated under sterile conditions throughout the cell growth period such as obtained by autoclaving or steam sterilization.

The cell culture apparatus of this invention also can be operated as a satellite flask in a series with other cell culture reactors by suitable tubing and pumping means. For example, the present apparatus can serve as a filtering means for a main cell culture flask used for the growth of the cells.

In an illustrative example of the present invention using a 4-liter capacity cell culture flask in accordance with the apparatus of FIGS. 1 to 4 described hereinbefore, in a cell culture run for over 65 hours at 250 rpm, the run was completed without any problems associated with cell disruption or filter clogging. Only a small amount of filter clogging occurred near the end of the run. Walker 256 Carcinosarcoma cells (ATCC NO. CCL 38) converted to suspension growth were thus grown to Dulbecco's Modified Minimum Essential Medium (with 4.5 mg/ml of glucose) supplemented with 6% fetal calf serum. The cells were seeded at less that $10^6$ cells per ml and reached a maximum of $8 \times 10^6$ cells per ml with a doubling time of 17.6 hours. More than 13 liters of media were passed through the filter during this run. Cells were healthy with high viability through a long period of log phase growth (more than 40 hours). These cells are useful for the production of tumor angiogenesis factor as is known from the publication by Folkman and Klagsburn in Chapter 31 of "Fundamental Aspects of Neoplasia", at pages 401–412, edited by Gottlieb et al, Springer-Verlag, N.Y., 1975.

It will be appreciated that the continuous cell culture system of this invention is adaptable to any of the well-known tissue culture media such as, for example, Basal Medium Eagle's (BME), Eagle's Minimum Essential Medium (MEM), Dulbecco's Modified Eagle Medium, Medium 199, and balanced salt solutions (BSS) such as those of Earle and Hanks fortified with various nutrients. These are commercially available tissue culture media and are described in detail by H. J. Morton, *In Vitro*, 6, 89–108 (1970). These conventional culture media contain known essential amino acids, mineral salts, vitamins and carbohydrates. They are also frequently fortified with mammalian sera such as fetal calf serum.

The present invention also is adaptable to all types of animal cells, including, for example, mammalian, fowl and amphibian cells, as well as plant cells, e.g. carrot cells. Primary cells taken from embryonic, adult or tumor tissues as well as cells of continuous cell lines can thus be used. Examples of typical such cells are primary rhesus monkey kidney cells, baby hamster kidney cells, pig kidney cells, embryonic rabbit kidney cells, mouse embryo fibroblasts, normal human lung embryo fibroblasts, HeLa cells, primary and secondary chick fibroblasts, and various cells transformed with SV-40 or polyoma virus. When using primary and non-continuous cell lines, it is generally preferable to include microcarriers in the culture medium for cell attachment.

Growth of these and other such cells in suitable nutrient culture media employing the continuous cell culture system of this invention can thereby be carried out in a manner to provide high cell densities without any moving bearing or seal surfaces contacting the cells which could cause cell disruption during the cell culture period and without any substantial clogging of the filter with cell debris.

Various other examples will be apparent to the person skilled in the art after reading of the disclosure herein without departing from the spirit and scope of the invention. All such further examples are included within the scope of the appended claims.

What is claimed is:

1. Apparatus for the continuous suspension culturing of cells comprising
    (A) a hollow flask having an opening at the top,
    (B) a stationary, hollow shaft means positioned within said flask, in fluid communication with said top opening of said flask and supported downwardly therefrom without any lower bearing,
    (C) a stationary filter unit supported downwardly from said shaft means without any lower bearing and without any moving seals between the filter unit and any filter support means which could contact the cell suspension, said filter having
        (1) a fluid collection cavity in direct fluid communication with the interior of said shaft means and the top of said flask, and
        (2) a porous peripheral surface having a pore size smaller than the cells to be cultured or the carrier particles upon which said cells are attached but sufficiently large to permit permeation of fluid into said fluid collection cavity, and
    (D) a rotatable agitator means concentrically disposed about said filter unit for rotation by suspension from sleeve bearing means having low-friction engagement with said hollow shaft means.

2. The apparatus of claim 1 in which the agitator means comprises a double helical blade closely surrounding the filter substantially over its entire length.

3. The apparatus of claim 1 in which the agitator means comprises a plurality of elongated, flat blades which are substantially equidistantly spaced apart circumferentially radiating inwardly toward the outer sidewall of the filter with clearance between said blades and said sidewall, and which extend substantially throughout the entire length of the filter.

4. The apparatus of claim 1 in which the sleeve bearing means comprises an inner sleeve having frictional engagement with said hollow shaft means, an outer sleeve having low-friction engagement with said inner sleeve and a flanged bearing seat positioned intermediate said filter unit and said pair of sleeves.

5. In the method of continuous cell culture comprising growing animal cells in an agitated liquid suspension of nutrient culture medium containing amino acids, mineral salts, vitamins and carbohydrates and periodically removing filtered liquid from the cells, the improvement comprising carrying out the agitation and filtering without any moving bearing or seal surfaces contacting said cells which could cause cell disruption and with agitator means concentrically disposed about the filter for rotation to substantially prevent any clogging of said filter with cell debris.

* * * * *